(12) United States Patent
Ferrari

(10) Patent No.: US 8,119,600 B2
(45) Date of Patent: Feb. 21, 2012

(54) COMPOSITIONS CONTAINING LYSOZYME AND C-1/C-4 POLYSACCHARIDES AND USE THEREOF IN ORAL CARE, COSMETOLOGY AND DERMATOLOGY, CONTRACEPTION, UROLOGY AND GYNECOLOGY

(76) Inventor: Stefano Ferrari, Rhinebeck, NY (US)

( * ) Notice: Subject to any disclaimer, the term of this patent is extended or adjusted under 35 U.S.C. 154(b) by 139 days.

(21) Appl. No.: 12/100,091

(22) Filed: Apr. 9, 2008

(65) Prior Publication Data

US 2008/0254079 A1  Oct. 16, 2008

Related U.S. Application Data

(60) Provisional application No. 60/910,880, filed on Apr. 10, 2007.

(51) Int. Cl.
*A61K 38/00* (2006.01)
*C07K 1/00* (2006.01)
(52) U.S. Cl. .................. 514/18.7; 530/324; 530/350
(58) Field of Classification Search .................. 424/401
See application file for complete search history.

(56) References Cited

U.S. PATENT DOCUMENTS

| 5,498,421 | A | * | 3/1996 | Grinstaff et al. | ............... 424/450 |
| 5,592,949 | A | * | 1/1997 | Moench et al. | ............... 128/837 |
| 5,928,928 | A | * | 7/1999 | Aerts | ............... 435/201 |
| 2004/0235770 | A1 | * | 11/2004 | Davis et al. | ............... 514/44 |

* cited by examiner

*Primary Examiner* — Sreeni Padmanabhan
*Assistant Examiner* — Timothy E Betton
(74) *Attorney, Agent, or Firm* — Norris McLaughlin & Marcus, P.A.

(57) ABSTRACT

A composition comprising a content of a lysozyme and a content of a C-1/C-4 polysaccharide is useful in oral care, cosmetology and dermatology, contraception, urology and gynecology. It is emphasized that this abstract is provided to comply with the rules requiring an abstract which will allow a searcher or other reader quickly to ascertain the subject matter of the technical disclosure. It is submitted with the understanding that it will not be used to interpret or limit the scope or meaning of the appended issued claims. 37 CFR §1.72(b).

4 Claims, No Drawings

COMPOSITIONS CONTAINING LYSOZYME AND C-1/C-4 POLYSACCHARIDES AND USE THEREOF IN ORAL CARE, COSMETOLOGY AND DERMATOLOGY, CONTRACEPTION, UROLOGY AND GYNECOLOGY

BACKGROUND OF THE INVENTION

1. Field of the Invention

The present invention relates generally to novel compositions and use thereof in oral care, cosmetology and dermatology, contraception, urology and gynecology.

2. Description of Related Art

Lysozymes constitute a group of enzymes capable of lysing the cell walls of bacteria and other microbes. For this reason, lysozymes have been widely used as food additives and for other purposes. The major source of commercially produced lysozyme is hen's egg white, which, although in widespread use, is theoretically capable of causing allergic reactions in some humans. Thus, recently, human recombinant lysozyme has been produced.

Chitosan and pullulan are well known polysaccharides. Chitosan has many industrial, medical, pharmaceutical, and nutritional uses, including applications as anticoagulants, antiviral agents, drug carriers, cosmetic additives, dialysis membranes, orthopedic materials, wound dressings, food stabilizers and thickeners, flavor and nutrient carriers, and dietary fiber, among other uses. Likewise, pullulan is also widely used, for example, in pharmaceutical, veterinary, food, cosmetic or other products like films for wrapping food, aspics or jellies, and for predosed formulations like soft or hard capsules.

BRIEF SUMMARY OF THE INVENTION

In a first embodiment, the present invention relates to a composition comprising both a content of a lysozyme and a content of a C-1/C-4 polysaccharide.

The term "lysozyme" as used herein denotes the family of enzymes that catalyze the hydrolysis of certain mucopolysaccharides of bacterial cell walls, and cause bacterial lysis. The term "lysozyme" includes naturally-occurring lysozymes, such as hen egg white lysozyme, synthetic lysozymes and recombinant lysozymes, such as human recombinant lysozyme, as well as lysozyme salts, such as are obtained with organic and inorganic acids, especially physiologically acceptable acids, as, for example, chloridic, sulfuric, phosphoric, lactic, acetic, malic, fumaric, citric, ascorbic acids, alone or in combination.

The term "C-1/C-4 polysaccharide" as used herein means a polysaccharide polymer comprised of a plurality of monosaccharide units, wherein at least one of the monosaccharide units is bonded through its C-1 position to the C-4 position of a second of the monosaccharide units.

In a second embodiment, the present invention relates to a method for caring for the oral cavity of a patient in need thereof, which involves introducing to said oral cavity or applying to an article to be introduced into said oral cavity an effective amount therefor of the inventive composition.

In a third embodiment, the present invention relates to a method for caring for the skin of a patient in need thereof, comprising topically applying to said skin an effective amount therefor of the inventive composition.

In a fourth embodiment, the present invention relates to a method of reducing the transmission of communicable diseases during sexual contact between two or more persons, comprising applying an effective amount therefor of the inventive composition to the sexual organs of at least one of said two or more persons and/or to an accessory protective element to be utilized during said sexual contact.

DETAILED DESCRIPTION OF THE INVENTION

The inventive composition comprises a content of a lysozyme and a content of a C-1/C-4 polysaccharide. As noted above, lysozymes can be naturally-occurring, synthetic or recombinant. In principal, all lysozymes are useful in the inventive composition, although the intended use of the inventive composition may suggest to those skilled in the art a preference for one type of lysozyme as opposed to another. In one preferred embodiment, the lysozyme is a human recombinant lysozyme. In another preferred embodiment, the lysozyme is a non-human lysozyme, especially a hen egg white lysozyme.

Likewise, all C-1/C-4 polysaccharides are useful in the inventive composition, although the intended use of the inventive composition may suggest to those skilled in the art a preference for one type of C-1/C-4 polysaccharide as opposed to another. In one preferred embodiment, the C-1/C-4 polysaccharide is selected from the group consisting of chitosan and pullulan. In a particularly preferred embodiment, the C-1/C-4 polysaccharide is chitosan. The term "chitosan" as used herein refers to poly-(1→4)-β-D-glucosamine, and is inclusive of deacetylated chitin, for example, obtained by enzymatic or chemical hydrolysis, as well as the addition compounds thereof, for example, obtained with organic and inorganic acids, especially physiologically acceptable acids, for example, lactic, acetic, malic, sorbic, benzoid, glycolic, accrilic, succinic, ossalic, tartaric, citric, ascorbic acids, etc., alone or in combination. Pullulan is a linear glucan produced by the so-called "black yeast" which belongs to the Deuteromycetes. The term "pullulan" as used herein refers not only to this material, but also the addition compounds thereof, for example, obtained with organic and inorganic acids, especially physiologically acceptable acids, for example, lactic, acetic, malic, sorbic, benzoid, glycolic, accrilic, succinic, ossalic, tartaric, citric, ascorbic acids, etc., alone or in combination. All the C-1/C-4 polysaccharides used according to the present invention are commercially available or readily obtainable according to well known synthetic techniques.

The concentration of lysozyme and of C-1/C-4 polysaccharide depends on the formulation and its use. For example, in a powder formulation containing only the active ingredients, the concentration of lysozyme ranges between 0.005% and 99.995% by weight based on the total weight of the composition, preferably the concentration of lysozyme could be comprised between 0.05% and 99.95% by weight. In the same composition, the concentration of the C-1/C-4 polysaccharide, for example chitosan and/or pullulan could be between 0.005% and 99.995% by weight, preferably between 0.05% and 99.95% by weight. A powder so formulated could be beneficially and conveniently applied, for instance, in the topical treatment of sores, burns and wounds.

In addition to the lysozyme content and the C-1/C-4 polysaccharide content, the inventive composition can include one or more additional active agents. In a preferred embodiment, the inventive composition includes one or more additional active agents selected from the group consisting of the family of transferring proteins, such as lactoferrin and ovotransferrin; the enzyme family of peroxidase, such hydrogen peroxide; a cysteine protease, such as papain; a serin protease, such as trypsin; organic acids such lipoinc acid; vitamins, such as vitamin A, D, E, C (ascorbic acid), the B group, folic acid, pantotenic acid; and minerals, such as zinc. In one especially preferred embodiment, the additional active agent is lactoferrin. In another especially preferred embodiment, the additional active agent is peroxidase. In a further especially preferred embodiment, the additional active agent is papain, etc. The amount of the active agent included in the composition depends on the intended application. For example, the active ingredient can be present in the composition in an amount that is 0.01 to 10 times the amount of lysozyme and chitosan or pullulan in the composition. For instance, a 25 gram pomade could contain as active ingredients 20 mg lysozyme, 200 mg chitosan and 100-1000 mg papain.

The inventive composition can be formulated in any one of a large number of suitable forms. In one preferred embodiment, the inventive composition is in the form of a tablet, lozenge, pill, capsule, chewing-gum, effervescent tablet and sachet, cream, lotion, powder, gel, mask, sprayable or injectable solution, sponge, hydrosoluble and/or edible film, strip, dental floss or interdental brush, lipstick, lip balm, lip gel or lip gloss, or wound dressing, etc. Edible products can include one or more flavoring agents, for example, mint, cherry, citrus or fruit flavors. In one especially preferred embodiment, the inventive composition is in the form of a topical cream, lotion or gel. In another especially preferred embodiment, the inventive composition is in the form of a sprayable or aerosol solution. In another especially preferred embodiment, the inventive composition is in the form of a hydrosoluble and/or edible film. In this especially preferred embodiment, the hydrosoluble and/or edible film optionally further includes one or more flavoring agents of the type indicated above. In another especially preferred embodiment, the inventive composition is in the form of a lipstick, lip balm, lip gel or lip gloss, any of which can, as indicated above, also include a flavoring agent.

The inventive composition finds usefulness in a variety of end uses. The inventive composition is useful in one embodiment in oral care. In this embodiment, the inventive composition is introduced into the oral cavity or applied to an article that is to be introduced into the oral cavity. In this embodiment, the amount of actives again depends on the application and the unit dosage form. For example, a therapeutically effective gum that is 16 mm in diameter and 1,750 mg in weight could contain from 10 mg to 50 mg lysozyme and from 50 mg to 90 mg of chitosan and/or pullulan. A film strip could contain from 1-3 mcg of lysozyme and from 3-5 mcg of chitosan and/or pullulan. Again, the exact amounts for any intended application will be determined empirically based on any number of factors well known to persons skilled in the art.

In a preferred embodiment, the inventive composition is in the form of a hydrosoluble and/or edible film, and this film is introduced into the oral cavity to improve the user's breath and/or to prevent or treat an oral infection. In an especially preferred embodiment, the oral infection is herpetic stomatitis. In another preferred embodiment the oral infection is gingivitis. In a third preferred embodiment the oral infection is aphtous ulcers.

In another preferred embodiment, the hydrosoluble and/or edible film includes one or more flavoring agents. All flavoring agents are suitable for this purpose. Especially preferred are mint flavors, and fruit flavors, particularly, peach and citrus fruits In a particularly preferred embodiment, the hydrosoluble and/or edible film includes a mint and/or peach flavoring.

In another oral care embodiment, the inventive composition is in the form of one or more strips, and these are applied to the gum and/or the inside of the cheeks to treat a localized disease. In an especially preferred embodiment, the localized disease is a canker sore, which is also known as an aphtous ulcer.

In another oral care embodiment, the inventive composition is in the form of a film-forming solution and/or spray, which is applied to an article to be introduced into said oral cavity in order to protect, clean and/or sanitize said article. In an especially preferred embodiment, this article is a removable dental product, for example, a retainer or denture.

This inventive compositions can also be topically applied to the skin for caring for the skin. For this purpose, in one preferred embodiment, the inventive composition is in the form of a cream, lotion or hydrosoluble film.

In one skin care embodiment, the inventive composition is applied to the skin of a patient suffering from a skin infection. In an especially preferred embodiment, the skin infection is acne, in particular, acnes resulting from infection by *Propionibacterium acne.*

In another skin care embodiment, the inventive composition is in the form of a wound dressing, which is applied to wounded skin, for example, to aid in healing of the wound. In an especially preferred embodiment, the wound dressing is a wet wound dressing, for example, a hydrocolloid or hydrogel. In a particularly preferred embodiment, the hydrocolloid or hydrogel includes a content of a proteolytic enzyme, preferably papain.

In another skin care embodiment, the inventive composition is in the form of a lipstick lip balm, lip gel or lip gloss, and the composition is applied to the lips. In an especially preferred embodiment, the patient suffers from a localized lip infection, for example, a cold sore or herpes labialis, and the inventive composition is applied to the lips as a treatment for such localized lip infection.

Another embodiment of the present invention relates to a method of reducing the transmission of communicable diseases during sexual contact between two or more persons. The method involves applying an effective amount therefor of the inventive composition to the sexual organs of at least one of said two or more persons and/or to an accessory protective element to be utilized during said sexual contact. In one preferred embodiment, the inventive composition is applied directly to the sex organs of at least one of said two or more persons. In another preferred embodiment, an accessory protective element is utilized, and the composition is applied directly to said accessory protective element. In one especially preferred embodiment, the accessory protective element is a condom or a contraceptive sponge. In this particular embodiment, the inventive composition preferably includes a content of lactoferrin.

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:

1. A method of reducing the transmission of communicable diseases during sexual contact between two or more persons, comprising applying an effective amount therefor of a composition comprising lactoferrin, chitosan, and lysozyme to the sexual organs of at least one of said two or more persons and/or to an accessory protective element to be utilized during said sexual contact.

2. The method according to claim 1, wherein the composition is applied directly to the sex organs of at least one of said two or more persons.

3. The method according to claim 1, wherein an accessory protective element is utilized, and the composition is applied directly to said accessory protective element.

4. The method according to claim 3, wherein said accessory protective element is a condom or a contraceptive sponge.

* * * * *